US012702687B2

(12) United States Patent
Chin

(10) Patent No.: US 12,702,687 B2
(45) Date of Patent: Aug. 11, 2026

(54) **PHARMACEUTICAL COMPOSITION FOR PREVENTING OR TREATING CHOLESTATIC LIVER INJURY COMPRISING *LEUCONOSTOC CITREUM* STRAIN AS ACTIVE INGREDIENT**

(71) Applicant: LISCure Bio Inc., Seongnam-si (KR)

(72) Inventor: Hwa Sup Chin, Yongin-si (KR)

(73) Assignee: LISCure Bio Inc., Seongnam-si (KR)

( * ) Notice: Subject to any disclaimer, the term of this patent is extended or adjusted under 35 U.S.C. 154(b) by 266 days.

(21) Appl. No.: 18/276,133

(22) PCT Filed: Feb. 7, 2022

(86) PCT No.: PCT/KR2022/001871

§ 371 (c)(1), (2) Date: Aug. 7, 2023

(87) PCT Pub. No.: WO2022/169338

PCT Pub. Date: Aug. 11, 2022

(65) Prior Publication Data

US 2024/0122996 A1 Apr. 18, 2024

(30) Foreign Application Priority Data

Feb. 8, 2021 (KR) ........................ 10-2021-0017842
Feb. 24, 2021 (KR) ........................ 10-2021-0014833

(51) Int. Cl.
*A61K 35/744* (2015.01)
*A61P 1/16* (2006.01)

(52) U.S. Cl.
CPC .............. *A61K 35/744* (2013.01); *A61P 1/16* (2018.01)

(58) Field of Classification Search
CPC .......................................................... A61P 1/16
See application file for complete search history.

(56) References Cited

U.S. PATENT DOCUMENTS

| | | | | |
|---|---|---|---|---|
| 2018/0169153 | A1 | 6/2018 | Berry et al. | |
| 2021/0008128 | A1 | 1/2021 | Nandakumar et al. | |
| 2022/0047652 | A1 | 2/2022 | Choi et al. | |
| 2023/0167401 | A1 | 6/2023 | Rawadi et al. | |
| 2024/0091281 | A1 * | 3/2024 | Chin | A61K 35/744 |

FOREIGN PATENT DOCUMENTS

| | | | |
|---|---|---|---|
| JP | 2006-296307 | A | 11/2006 |
| JP | 2018-537484 | A | 12/2018 |
| KR | 10-2032982 | B1 | 10/2019 |
| KR | 10-2020-0040277 | A | 4/2020 |
| KR | 10-2159630 | B1 | 9/2020 |
| WO | 2017/146213 | A1 | 8/2017 |
| WO | 2020/175940 | A1 | 9/2020 |
| WO | 2020/182916 | A1 | 9/2020 |

OTHER PUBLICATIONS

Hilscher et al., Mayo Clinic Proc., 2020; 95(10):2263-2279 (Year: 2020).*

Cleveland Clinic, https://my.clevelandclinic.org/health/diseases/24554-cholestasis, 2022 (Year: 2022).*

Sato et al., "Functional roles of gut bacteria imbalance in cholangiopathies", Liver Research, vol. 3, 2019, p. 40-45, https://doi.org/10.1016/j.livres.2018.11.001.

Timmerman et al., "Design of a multispecies probiotic mixture to prevent infectious complications in critically ill patients", Clinical Nutrition, vol. 26, 2007, pp. 450-459, doi: 10.1016/j.clnu. 2007.04.008.

Silva et al., "Probiotic properties of *Weissella cibaria* and *Leuconostoc citreum* isolated from tejuino—A typical Mexican beverage", LWT—Food Science and Technology, vol. 86, 2017, pp. 227-232, http://dx.doi.org/10.1016/j.lwt.2017.08.009.

Shimizu et al., "Successful Treatment of Primary Sclerosing Cholangitis with a Steroid and a Probiotic", Case Reports in Gastroenterology, vol. 6, May 8, 2012, pp. 249-253, DOI: 10.1159/000338834.

Extended European Search Report issued Jan. 24, 2025 in Application No. 22750087.3 supplemental.

Frank P. Vleggaar, et al., "Probiotics in primary sclerosing cholangitis: a randomized placebo-controlled crossover pilot study", European Journal of Gastroenterology & Hepatology, 2008, pp. 688-692, vol. 20, No. 7.

International Search Report for PCT/KR2022/001871 dated May 16, 2022 (PCT/ISA/210).

Written Opinion for PCT/KR2022/001871 dated May 16, 2022 (PCT/ISA/237).

Seung Kee Cho et al., "Development of Bile Salt-Resistant *Leuconostoc citreum* by Expression of Bile Salt Hydrolase Gene", J. Microbiol. Biotechnol., 2015, vol. 25, No. 12, pp. 2100-2105 (6 pages total).

Office Action issued Oct. 7, 2025 in Japanese Application No. 2023-547883.

* cited by examiner

*Primary Examiner* — Brian Gangle
*Assistant Examiner* — Lakia J Jackson-Tongue
(74) *Attorney, Agent, or Firm* — Sughrue Mion, PLLC

(57) ABSTRACT

The present invention relates to a composition comprising a *Leuconostoc citreum* strain or its culture as an active ingredient for preventing, improving or treating cholestatic liver injury, specifically primary biliary cirrhosis (PBC) and primary sclerosing cholangitis (PSC). According to the present invention, since the composition exhibits excellent preventive and therapeutic effects on various cholestatic liver injuries, the composition can be usefully used as a composition for the treatment, prevention, improvement, or the like of cholestatic liver injury in humans or animals.

3 Claims, 5 Drawing Sheets

Specification includes a Sequence Listing.

[FIG. 1]
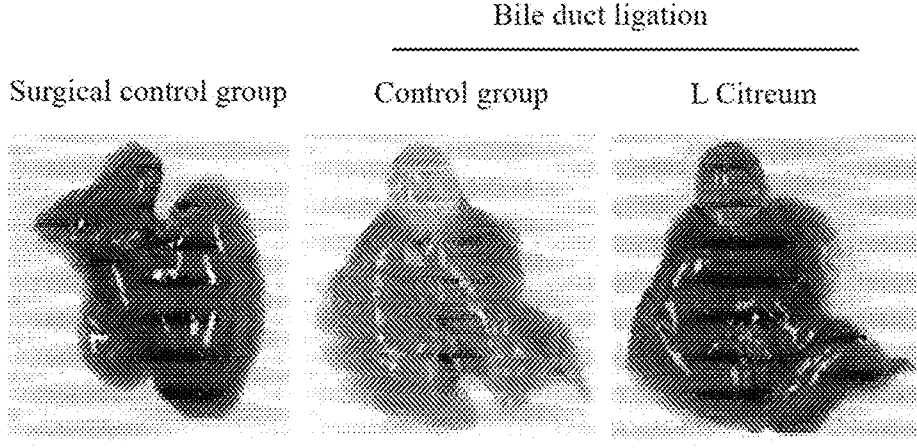
[FIG. 2]
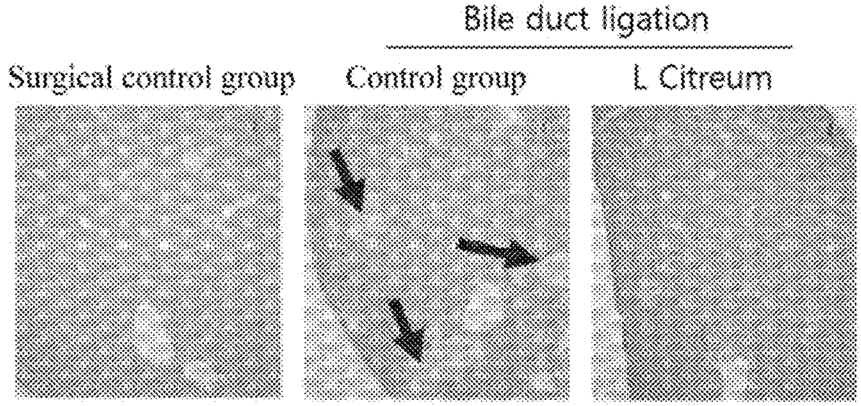
* hepatocellular necrosis part

[FIG. 3]
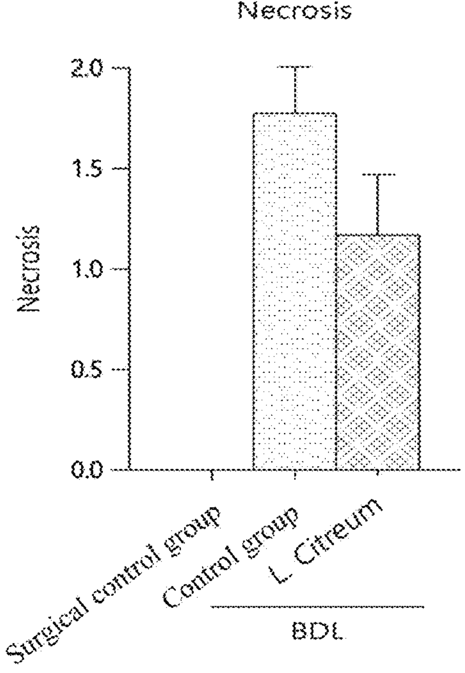

[FIG. 4]
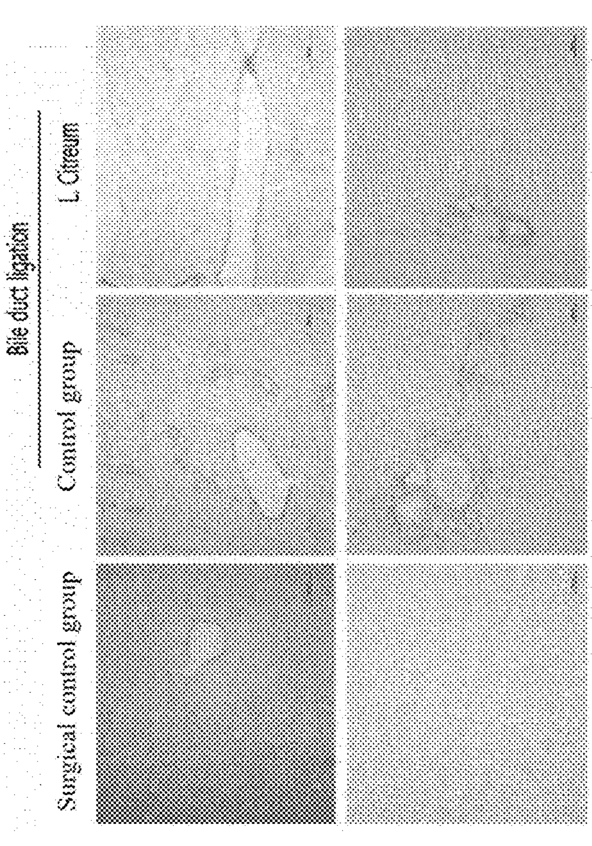

[FIG. 5]
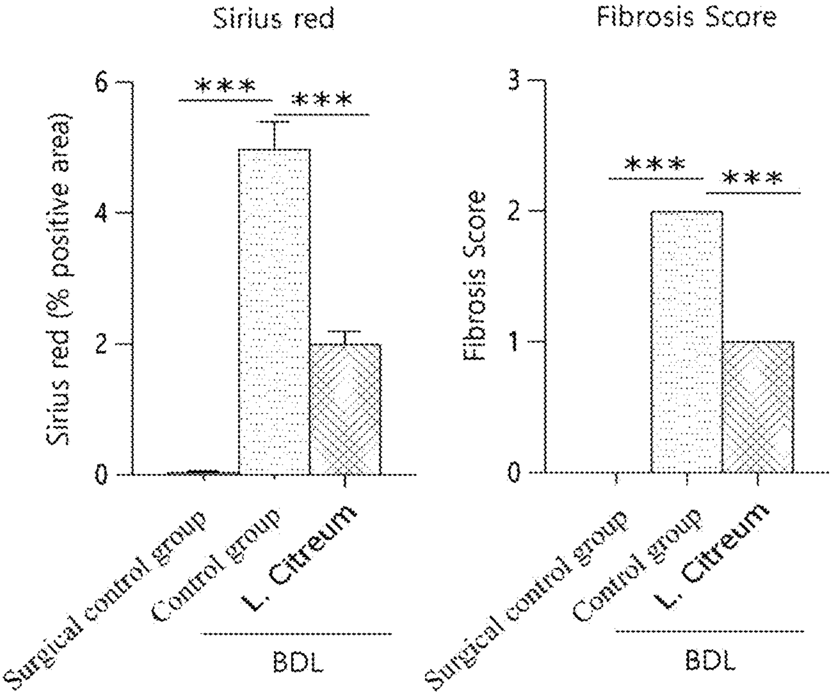
[FIG. 6]
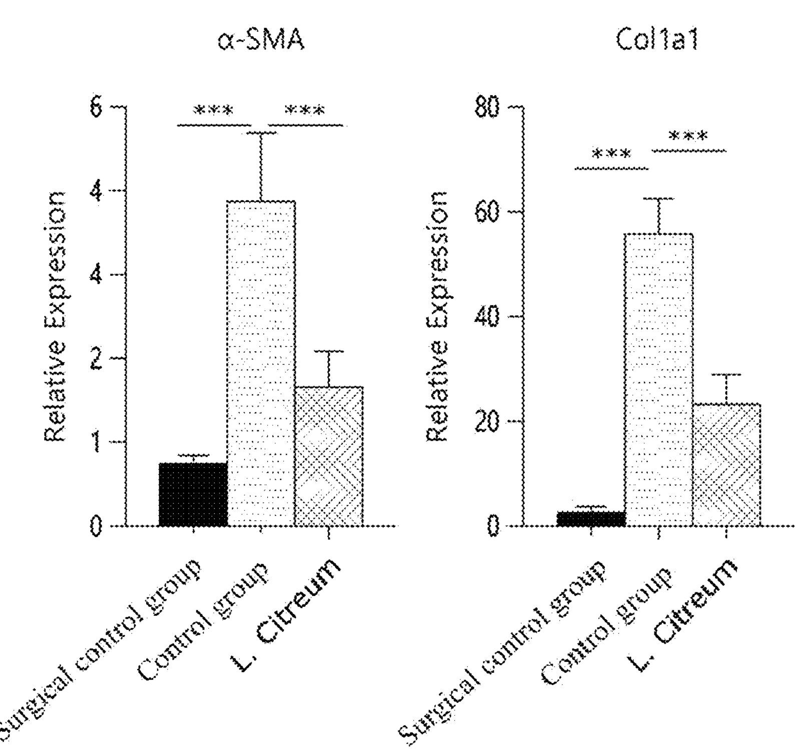

[FIG. 7]
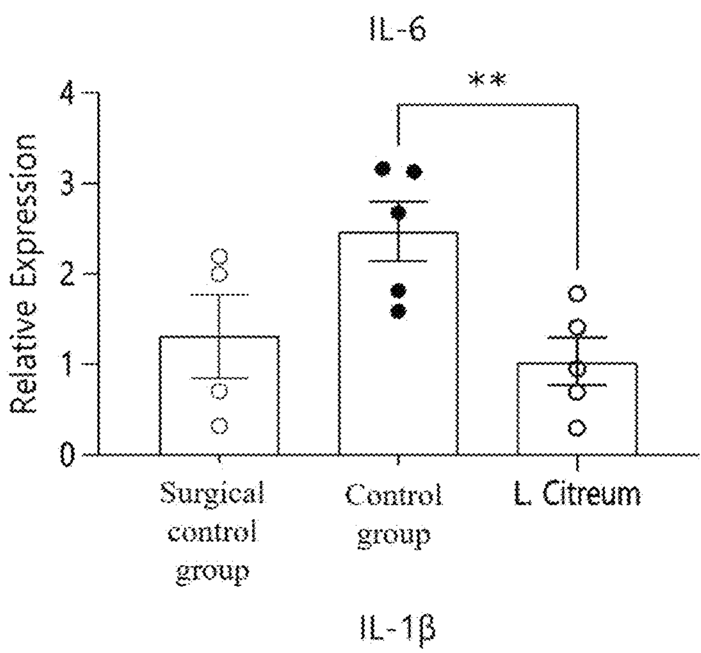
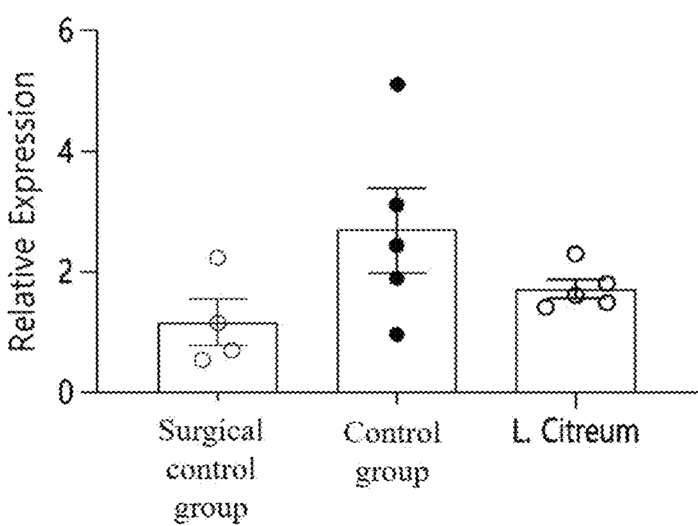

SEQUENCE LISTING

```
<160> NUMBER OF SEQ ID NOS: 1

<210> SEQ ID NO 1
<211> LENGTH: 1430
<212> TYPE: DNA
<213> ORGANISM: Leuconostoc citreum

<400> SEQUENCE: 1

gatgaacgct ggcggcgtgc ctaatacatg caagtcgaac gcgcagcgag aggtgcttgc     60

acctttcaag cgagtggcga acgggtgagt aacacgtgga taacctgcct caaggctggg    120

gataacattt ggaaacagat gctaataccg aataaaactt agtatcgcat gatatcaagt    180

taaaaggcgc tacggcgtca cctagagatg gatccgcggt gcattagtta gttggtgggg    240

taaaggctta ccaagacgat gatgcatagc cgagttgaga gactgatcgg ccacattggg    300

actgagacac ggcccaaact cctacgggag gctgcagtag ggaatcttcc acaatgggcg    360

caagcctgat ggagcaacgc cgcgtgtgtg atgaaggctt tcgggtcgta aagcactgtt    420

gtatgggaag aaatgctaaa atagggaatg attttagttt gacggtacca taccagaaag    480

ggacggctaa atacgtgcca gcagccgcgg taatacgtat gtcccgagcg ttatccggat    540

ttattgggcg taaagcgagc gcagacggtt gattaagtct gatgtgaaag cccggagctc    600

aactccggaa tggcattgga aactggttaa cttgagtgtt gtagaggtaa gtggaactcc    660

atgtgtagcg gtggaatgcg tagatatatg gaagaacacc agtggcgaag gcggcttact    720

ggacaacaac tgacgttgag gctcgaaagt gtgggtagca aacaggatta gataccctgg    780

tagtccacac cgtaaacgat gaatactagg tgttaggagg tttccgcctc ttagtgccga    840

agctaacgca ttaagtattc cgcctgggga gtacgaccgc aaggttgaaa ctcaaaggaa    900

ttgacgggga cccgcacaag cggtggagca tgtggtttaa ttcgaagcaa cgcgaagaac    960

cttaccaggt cttgacatcc tttgaagctt ttagagatag aagtgttctc ttcggagaca   1020

aagtgacagg tggtgcatgg tcgtcgtcag ctcgtgtcgt gagatgttgg gttaagtccc   1080

gcaacgagcg caacccttat tgttagttgc cagcattcag ttgggcactc tagcgagact   1140
```

-continued

```
gccggtgaca aaccggagga aggcggggac gacgtcagat catcatgccc cttatgacct   1200
gggctacaca cgtgctacaa tggcgtatac aacgagttgc caacctgcga aggtgagcta   1260
atctcttaaa gtacgtctca gttcggactg cagtctgcaa ctcgactgca cgaagtcgga   1320
atcgctagta atcgcggatc agcacgccgc ggtgaatacg ttcccgggtc ttgtacacac   1380
cgcccgtcac accatgggag tttgtaatgc ccaaagccgg tggcctaacc              1430
```

PHARMACEUTICAL COMPOSITION FOR PREVENTING OR TREATING CHOLESTATIC LIVER INJURY COMPRISING *LEUCONOSTOC CITREUM* STRAIN AS ACTIVE INGREDIENT

CROSS REFERENCE TO RELATED APPLICATIONS

This application is a National Stage of International Application No. PCT/KR2022/001871 filed Feb. 7, 2022, claiming priorities based on Korean Patent Application No. 10-2021-0017842 filed Feb. 8, 2021 and Korean Patent Application No. 10-2022-0014833 filed Feb. 4, 2022, the entire disclosures of which are incorporated herein by reference.

INCORPORATION BY REFERENCE OF SEQUENCE LISTING

The content of the electronically submitted sequence listing, file name: Q289713_sequence listing as filed.txt; size: 2,380 bytes; and date of creation: Aug. 7, 2023, filed herewith, is incorporated herein by reference in its entirety.

TECHNICAL FIELD

The present invention relates to a composition comprising a *Leuconostoc citreum* strain or its culture as an active ingredient for preventing, improving or treating cholestatic liver injury, specifically primary biliary cirrhosis (PBC) and primary sclerosing cholangitis (PSC).

BACKGROUND ART

Cholestatic liver injury is a disease caused by the accumulation of bile acids and lipids. The liver regulates central lipid metabolic processes including fatty acid synthesis, mitochondrial β-oxidation, and phospholipid transport. Injured bile secretion caused by biliary obstruction or liver damage hinders cholesterol and phospholipid metabolisms. In a bile duct ligation (BDL) rat model, a liver lipid concentration was not altered, whereas serum levels of very low-density lipoprotein (VLDL) cholesterol and low-density lipoprotein (LDL) cholesterol are significantly increased (T. Kamisako, et al., Hepatology Research, vol. 25, no. 2, pp. 99-104, 2003).

Although PBC, one of the cholestatic liver injuries, is a relatively rare disease that shows the features of chronic cholestatic disease, the PBC has attracted the attention of many gastroenterologists due to its characteristic clinical behaviors and pathophysiology. The PBC appears in all races and has a prevalence of 100 to 200 per 1 million population, and the age of onset is usually between 30 and 70 years, but is particularly affected in middle-aged women, and if there is a PBC patient in the family, it is known that the possibility of PBC patients appearing in female family is about 1000 times higher than in a control group. Various autoimmune diseases may be accompanied, and characteristically, anti-mitochondrial antibodies are found in most patients. Histologically, progressive nonsuppurative cholangitis is characterized.

In addition to the PBC, the PSC is a chronic cholestatic disease of an unknown cause and shows inflammatory fibrosis and destruction of the intrahepatic and extrahepatic biliary tracts, and has a characteristic well-associated with inflammatory bowel disease. The PSC progresses as in the PBC to cause cirrhosis and complications, but there is no effective medical treatment.

The exact cause of the PSC is not yet known, but has been considered to be involved with autoimmune reactions, hepatic portal vein bacteremia, genetic predisposition, and the like. In patients, the fact that several autoantibodies ANA, SMA, and ANCA are shown, complements and immune complexes are increased in the blood, and are well associated with inflammatory bowel disease suggests the possibility that an autoimmune mechanism may be a cause. The PSC has a high prevalence in patients' families, and HLA association is known in some cases, and genetic predisposition is thought to be involved in the pathogenesis. In people with the genetic predisposition, there has been disclosed a mechanism in which the hepatic portal vein bacteremia caused by inflammatory bowel disease, etc. occurs and then TNF-α secretion is increased by activated Kupffer cells to cause intrahepatic lesions, but the exact etiology has not yet been clearly elucidated (Clinical and Molecular Hepatology, Clinical and Molecular Hepatology Vol. 10, No. 3s pp. 36-53, 2004).

Recently, there is disclosed an effect of preventing or treating cholestatic liver injury by a composition including stem cells (Korean Patent Registration No. 10-2159630) and a formulation including a plurality of bacteria (US Patent Publication No. 2021-0008128), but there is no description about a preventive or therapeutic effect of cholestatic liver injury including a lactic acid bacteria-derived *Leuconostoc citreum* strain or its culture as an active ingredient.

Under this background, the present inventors studied to find substances for preventing and treating cholestatic liver injury using lactic acid bacteria with little toxicity and side effects, and as a result, confirmed that a *Leuconostoc citreum* strain or its culture had a preventive or therapeutic effect on primary biliary cirrhosis or primary sclerosing cholangitis, and then completed the present invention.

DISCLOSURE

Technical Problem

An object of the present invention is to provide a pharmaceutical composition for preventing or treating cholestatic liver injury comprising a *Leuconostoc citreum* strain as an active ingredient.

Further, another object of the present invention is to provide a food composition or food additive composition for preventing or improving cholestatic liver injury including a *Leuconostoc citreum* strain as an active ingredient.

Further, yet another object of the present invention is to provide a feed composition or feed additive composition for preventing or improving livestock cholestatic liver injury including a *Leuconostoc citreum* strain as an active ingredient.

Technical Solution

An aspect of the present invention provides a pharmaceutical composition for preventing or treating cholestatic liver injury including a *Leuconostoc citreum* strain or its culture as an active ingredient.

Further, another aspect of the present invention provides a food composition or food additive composition for preventing or improving cholestatic liver injury including a *Leuconostoc citreum* strain or its culture as an active ingredient.

Further, yet another aspect of the present invention provides a feed composition or feed additive composition for preventing or improving livestock cholestatic liver injury including a *Leuconostoc citreum* strain or its culture as an active ingredient.

Advantageous Effects

According to the present invention, since the *Leuconostoc citreum* strain or its culture exhibits excellent preventive and therapeutic effects on various cholestatic liver injuries, the *Leuconostoc citreum* strain or its culture may be usefully used as a composition for the treatment, prevention, improvement, or the like of cholestatic liver injury in humans or animals.

DESCRIPTION OF DRAWINGS

FIG. 1 is a diagram showing a photograph of observing hepatic tissues of mice sacrificed after treating a *Leuconostoc citreum* WiKim0104 strain in a Bile duct ligation-induced animal model.

FIG. 2 is a diagram showing a photograph of observing the hepatic necrosis of hepatic tissues of mice sacrificed through H&E staining after treating a *Leuconostoc citreum* WiKim0104 strain in a Bile duct ligation-induced animal model.

FIG. 3 is a diagram showing a graph of evaluating the cell necrosis degree of hepatic tissues of mice sacrificed after treating a *Leuconostoc citreum* WiKim0104 strain in a Bile duct ligation-induced animal model.

FIG. 4 is a diagram showing a photograph of observing the hepatocellular fibrosis of hepatic tissues of mice sacrificed through sires red staining after treating a *Leuconostoc citreum* WiKim0104 strain in a Bile duct ligation-induced animal model.

FIG. 5 is a diagram showing a graph of evaluating sires red % positive areas and fibrosis scores of hepatic tissues of mice sacrificed after treating a *Leuconostoc citreum* WiKim0104 strain in a Bile duct ligation-induced animal model.

FIG. 6 is a diagram showing a graph of measuring α-SMA and Col1a1 expression levels using cDNA synthesized from RNA isolated from hepatic tissues of mice sacrificed after treating a *Leuconostoc citreum* WiKim0104 strain in a Bile duct ligation-induced animal model.

FIG. 7 is a diagram showing a graph of measuring IL-6 and IL-1β expression levels using cDNA synthesized from RNA isolated from hepatic tissues of mice sacrificed after treating a *Leuconostoc citreum* WiKim0104 strain in a Bile duct ligation-induced animal model.

BEST MODE

A composition including a *Leuconostoc citreum* strain of the present invention or its culture as an active ingredient has a preventive or therapeutic effect of cholestatic liver injury, and may be used as a pharmaceutical composition.

The *Leuconostoc citreum* strain of the present invention is a lactic acid bacteria strain. The *Leuconostoc citreum* strain is a probiotic, and has general intestinal regulating and immune enhancing effects of lactic acid bacteria. It is a well-known fact that lactic acid bacteria in *Leuconostoc* sp. have an intestinal regulating effect and an immune enhancing effect.

The *Leuconostoc citreum* strain may be a *Leuconostoc citreum* WiKim0104 strain, and has a nucleic acid sequence represented by SEQ ID NO: 1.

The *Leuconostoc citreum* strain may be inoculated in 0.1 to 10% of a MRS liquid medium and cultured and used at 25 to 37° C. for 4 to 48 hours.

The culturing method is preferably a static culture method, but is not limited thereto.

In the present invention, the 'probiotics' is understood as the meaning of 'a living microorganism that has a beneficial effect on the health of the host by improving an intestinal microbial environment of the host in the gastrointestinal tract of animals, including humans'. The probiotics are live microorganisms with probiotic activity, which may have a beneficial effect on the intestinal flora of the host, when fed to humans or animals in the form of dried cells or fermentation products in the form of single or multiple strains.

The cholestatic liver injury may be pulmonary cholestatic liver injury, renal cholestatic liver injury or hepatic cholestatic liver injury, but is not limited thereto.

The *Leuconostoc citreum* strain included in the composition according to the present invention may exist as live or dead cells, and may also exist in a dried or freeze-dried form. In addition, a culture of the *Leuconostoc citreum* strain may be an active ingredient, and the culture may include a live cell culture medium or a dead cell supernatant. Types of lactic acid bacteria suitable to be included in various compositions and formulation methods are well known to those skilled in the art.

The composition may be administered orally or parenterally. In the case of parenteral administration, the composition may be administered by intravenous injection, subcutaneous injection, intramuscular injection, intraperitoneal injection, intradermal administration, topical administration, intranasal administration, intrapulmonary administration, intrarectal administration, etc., and preferably intravenous injection, but it is not limited thereto.

A suitable dose of the composition may be variously prescribed by factors, such as a formulation method, an administration type, age, weight, and sex of a patient, a pathological condition, food, an administration time, an administration route, an excretion rate, and response susceptibility.

When the composition of the present invention is used as a pharmaceutical composition, the pharmaceutical composition of the present invention may be prepared by using pharmaceutically suitable and physiologically acceptable adjuvants in addition to the active ingredients. As the adjuvants, excipients, disintegrants, sweeteners, binders, coating agents, expanding agents, lubricants, slip modifiers, flavoring agents, or the like may be used.

The pharmaceutical composition may be preferably formulated by further including at least one kind of pharmaceutically acceptable carrier in addition to the above-described active ingredients for administration.

For example, for formulation in the form of tablets or capsules, the active ingredient may be combined with an oral, a non-toxic pharmaceutically acceptable inert carrier such as ethanol, glycerol, water, or the like. Further, if desired or necessary, suitable binders, lubricants, disintegrants and coloring agents may also be included as a mixture. The suitable binders are not limited thereto, but include natural sugars such as starch, gelatin, glucose or beta-lactose; natural and synthetic gums such as acacia, tragacanth or sodium oleate; sodium stearate, magnesium stearate, sodium benzoate, sodium acetate, sodium chloride and the like. The disintegrant is not limited thereto, but includes starch, methylcellulose, agar, bentonite, xanthan gum, or the like. In the composition formulated with a liquid solution, the pharmaceutically acceptable carrier is suitable for sterilized and living bodies and may use saline, sterilized water, ringer's solution, buffered saline, albumin injection solution, dextrose solution, maltodextrin solution, glycerol, ethanol, and a mixture of at least one of these ingredients, and if necessary, may add other general additives such as antioxidants, buffers, and bacteriostatic agents. In addition, the composition may be prepared in injectable formulations such as aqueous solutions, suspensions, and emulsions, pills, capsules, granules, or tablets by further adding a diluent, a dispersant, a surfactant, a binder, and a lubricant.

Furthermore, as a suitable method in the field, the composition may be formulated preferably according to each disease or ingredient using a method disclosed in Remington's Pharmaceutical Science, Mack Publishing Company, Easton PA.

A composition including a *Leuconostoc citreum* strain of the present invention or its culture as an active ingredient may be used as a food composition or food additive composition for preventing or improving cholestatic liver injury.

The food composition may be a health functional food form.

The "functional health food" refers to food prepared and processed using raw materials or ingredients that have functionality useful to the human body in accordance with the Health Functional Food Act (Article 3 (1)), and the "functionality" means regulating nutrients for the structure and function of the human body or obtaining useful effects for health uses such as physiological functions (Article 3 (2)).

The food composition may further include a food additive, and compliance as the "food additive" is determined by the specifications and standards for the corresponding item in accordance with the General Rules of the Korea Food Additives Code and general test methods approved by the Ministry of Food and Drug Safety, unless otherwise specified.

The items disclosed in the "Korea Food Additives Code" may include, for example, chemical composites such as ketones, glycine, potassium citrate, nicotinic acid, and cinnamic acid; natural additives such as persimmon pigment, licorice extract, crystalline cellulose, and guar gum; mixed formulations such as sodium L-glutamate formulations, noodle-added alkali agents, preservative formulations, tar color formulations, etc.

Foods containing the active ingredient of the present invention may include confectionery such as bread, rice cakes, dried confectionery, candy, chocolate, chewing gum, and jam; ice cream products such as ice cream, frozen confectionery, and ice cream powder; dairy products such as milk, low-fat milk, lactose-degraded milk, processed milk, goat milk, fermented milk, butter milk, concentrated milk, milk cream, butter milk, natural cheese, processed cheese, powdered milk, and whey; meat products such as processed meat products, processed egg products, and hamburgers; fish meat products such as fish cake, ham, sausage, bacon, etc.; noodles such as ramen, dried noodles, fresh noodles, fried noodles, deluxe dried noodles, improved soft noodles, frozen noodles, and pasta; drinks such as fruit drinks, vegetable drinks, carbonated drinks, soy milk, *lactobacillus* drinks such as yogurt, and mixed drinks; seasoned foods such as soy sauce, soybean paste, gochujang, chunjang, cheonggukjang, mixed soy sauce, vinegar, sauces, tomato ketchup, curry, and dressing; margarine, shortening and pizza, but are not limited thereto.

In addition, the composition of the present invention may include various nutrients, vitamins, electrolytes, flavoring agents, coloring agents, pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. In addition, the composition of the present invention may include pulps for preparing natural fruit juices, fruit juice beverages or vegetable beverages. These ingredients may be used independently or in combination.

The beverage composition including the active ingredient of the present invention is not particularly limited in other ingredients, and may contain various flavoring agents, natural carbohydrates, or the like as additional ingredients like conventional beverages. Examples of the above-mentioned natural carbohydrates may include general sugars, such as monosaccharides (e.g., glucose, fructose and the like); disaccharides (e.g., maltose, sucrose and the like); and polysaccharides (e.g., dextrin, cyclodextrin and the like), and sugar alcohols such as xylitol, sorbitol, erythritol, and the like. As flavoring agents other than those described above, natural flavoring agents (thaumatin, stevia extract (e.g., Rebaudioside A, glycyrrhizin etc.)) and synthetic flavoring agents (saccharin, aspartame, etc.) may be advantageously used.

Further, a composition including a *Leuconostoc citreum* strain of the present invention or its culture as an active ingredient may be used as a feed composition or feed additive composition for preventing or improving livestock cholestatic liver injury.

When the composition is prepared as a feed additive, the composition may be prepared in the form of 20 to 90% high-concentrate or powder or granules. The feed additive may further include any one or one or more of organic acids such as citric acid, fumaric acid, adipic acid, lactic acid, and malic acid, phosphates such as sodium phosphate, potassium phosphate, acidic pyrophosphate, and polyphosphate, or natural antioxidants such as polyphenol, catechin, alpha-tocopherol, rosemary extract, vitamin C, green tea extract, licorice extract, chitosan, tannic acid, phytic acid, and the like. When prepared as a feed, the composition may be formulated in a conventional feed form, and may include general feed ingredients together.

The feed and the feed additives may further include grains, such as milled or ground wheat, oats, barley, corn and rice; vegetable protein feeds, such as feeds based on rape, soybean, and sunflower as a main ingredient; animal protein feeds, such as blood meal, meat meal, bone meal and fish meal; sugar and dairy products, such as dry ingredients consisting of various powdered milk and whey powder, and in addition, nutritional supplements, digestion and absorption enhancers, growth promoters, and the like may be further included.

The feed additive may be administered to animals alone or also administered in combination with other feed additives in an edible carrier. In addition, the feed additives may be easily administered to animals as a top dressing, directly mixed with animal feed, or in an oral formulation separate from feed. When the feed additive is administered separately from animal feed, the feed additive may be prepared as an immediate release or sustained release formulation in combination with a pharmaceutically acceptable edible carrier, as well-known in the art. Such edible carriers may be solids or liquids, for example corn starch, lactose, sucrose, soybean flakes, peanut oil, olive oil, sesame oil and propylene glycol. When the solid carrier is used, the feed additive may be tablets, capsules, powder, troches or sugar-containing tablets or microdispersible top dressing. When the liquid carrier is used, the feed additive may be formulations of gelatin soft capsules, syrups, suspensions, emulsions, or solution formulations.

In addition, the feed and the feed additive may contain auxiliary agents, such as preservatives, stabilizers, wetting agents or emulsifying agents, solution accelerators, and the like. The feed additive may be used to be added to an animal feed by steeping, spraying or mixing.

The feed or feed additive of the present invention may be applied to a plurality of animal diets including mammals, poultry and fish.

The mammals may be used for pigs, cows, horses, sheep, rabbits, goats, rats, hamsters, and guinea pigs, which are rodents and laboratory rodents, as well as pets (e.g., dogs and cats). The poultry may also be used for chickens, turkeys, ducks, geese, pheasants, and quails. The fish may be used for carp, crucian carp, trout, etc., but the present invention is not limited thereto.

Modes

Hereinafter, the present invention will be described in more detail through Examples. These Examples are to explain the present invention in more detail, and it will be apparent to those skilled in the art that the scope of the present invention is not limited by these Examples in accordance with the gist of the present invention.

Example 1. Culture of Strain

A *Leuconostoc citreum* WiKim0104 (accession number KCCM12420P) strain was distributed with the permission of the depositor, Korea Food Research Institute, and experiments were conducted.

The distributed *Leuconostoc citreum* WiKim0104 strain was inoculated at 1% in 30 ml of an MRS liquid medium and static cultured at 30° C. for 18 hours. After incubation, the culture solution was stored separately by centrifugation at 3000 rpm for 10 minutes, and the cells were washed three times with a phosphate buffered saline (PBS) solution to remove the remaining medium component.

Example 2. Confirmation of Bile Accumulation Inhibitory Effect in Animal Model

2-1. Experimental Animal Mouse Conditions

An experimental animal used in the experiment was supplied with male 8-week-old C57BL6 mice, and bred during an experimental period after a one-week stabilization period in an animal breeding room under an SPF environment maintained at a room temperature of 20±2° C. and a humidity of 55±15%. As a feed, a general pellet feed without adding antibiotics was supplied, water was allowed to be consumed at any time, and the experiment was performed after adapting to a diet for 1 week.

2-2. Construction of Bile Duct Ligation-Induced Animal Model

The accumulation of cytotoxic bile in hepatocytes was a major cause of cholestatic liver injury, such as primary biliary cirrhosis (PBC) and primary sclerosing cholangitis (PSC). Bile duct ligation was performed to confirm the efficacy of a *Leuconostoc citreum* strain for cholestatic liver injury.

The bile duct of the mouse prepared in Example 2-1 was tied twice with a non-absorbable surgical thread. As a control group, the surgery was performed in the same manner without tying the bile duct. After surgery, the mice were grouped according to the Z array method based on changes in body weight, jaundice, and urine color on the day of drug administration. After grouping, the experimental group was orally administered with the *Leuconostoc citreum* WiKim0104 strain at $2\times10^9$ CFU/day once a day at 0.2 mL/head volume for 2 weeks. The control group ate the same amount of PBS. For all animals, general symptoms were observed once a day, and the presence or absence of moribund and dead animals was confirmed twice a day, and observation was conducted from post-surgery to the end of administration. 2 weeks of administration was terminated, and the mice were sacrificed.

2-3. Pathological Analysis of Hepatic Tissue

An autopsy was performed from the sacrificed mice prepared in 2-2 above, and tissue analysis was performed. A visual inspection was performed on the abdominal organs, the presence or absence of abnormalities in the internal organs was confirmed, and hepatic and intestinal tissues were extracted. The extracted hepatic tissues were washed with physiological saline and water was removed with a filter paper, and then the liver shapes were photographed and compared, and the result was illustrated in FIG. 1.

As illustrated in FIG. 1, it was confirmed that the liver color changed to yellow in a bile duct ligation-induced control group compared to a surgical control group, and the shape and color of the liver changed similar to those of the surgical control group, which was a normal mouse, according to administration of *Leuconostoc citreum.*

In addition, for histopathological examination, the hepatic tissues were fixed in 10% neutral formalin, and the fixed tissues were fabricated and microsectioned into paraffin blocks through a general tissue processing procedure such as trimming, dehydration, and paraffin embedding. The microsectioned tissue sections were subjected to Hematoxylin & Eosin (H&E) staining to histologically analyze hepatocyte necrosis, cholangiocyte proliferation, and portal edema, and the results were illustrated in FIGS. 2 and 3.

As illustrated in FIGS. 2 and 3, as a result of H&E staining, hepatocellular necrosis (arrow) was observed in a BDL model control group, and cholangiocyte proliferation was observed around the bile duct. In the *Leuconostoc citreum* strain treated group, it may be visually confirmed that hepatocyte necrosis was significantly reduced, and as a result of the histopathology score, the hepatocellular necrosis score was significantly decreased.

2-4. Evaluation of Hepatic Fibrosis by Cholestasis

Hepatic fibrosis analysis was performed using hepatocytes obtained from the sacrificed mice prepared in 2-2 above. As one of major pathological symptoms in cholestatic liver injury, hepatocyte necrosis and liver fibrosis were known, and thus in order to evaluate hepatic fibrosis due to cholestasis, graphs showing the fibrosis index through the result confirmed by sirus red staining and tissue pathology evaluation were shown in FIGS. 4 and 5.

As illustrated in FIG. 4, it was confirmed that the sirus red % positive area increased by BDL significantly decreased in the group treated with the *Leuconostoc citreum* strain. As illustrated in FIG. 5, it was confirmed that the fibrosis score increased by BDL significantly decreased in the group treated with the *Leuconostoc citreum* strain as compared with the control group.

2-5. Analysis of Expression Levels of Cytokines Related to Hepatic Fibrosis and Inflammation RNA was isolated from the hepatic tissue obtained from the sacrificed mice prepared in 2-2 above, and changes in α-SMA (alpha-smooth muscle actin) and Col1a1 (collagen type 1a), which were gene markers related to fibrosis and inflammation, were confirmed by a q-RT-PCR method. A mouse hepatic tissue of each group was added with 1 ml of trizol, the tissue was pulverized with a homogenizer, and then RNA was isolated using chloroform and isopropanol, and then cDNA was synthesized. Results of observing changes in fibrosis and inflammatory cytokines using the synthesized cDNA were shown in FIGS. 6 and 7.

As shown in FIG. 6, it was confirmed that the expression levels of α-SMA and Col1a1 were significantly reduced in the group treated with the *Leuconostoc citreum* strain compared to the BDL control group.

As shown in FIG. 7, it was confirmed that the expression levels of IL-6 and IL-1β were significantly reduced in the group treated with the *Leuconostoc citreum* strain compared to the BDL control group.

According to the results, it was confirmed that when the composition according to the present invention was treated, the composition exhibited excellent effects on hepatocellular damage, fibrosis and inflammation caused by bile accumulation, and may be used as a preventive and therapeutic composition for cholestatic liver injury.

ACCESSION NUMBER

Depositary Authority Name: Korean Culture Center of Microorganisms (Overseas)
Accession number: KCCM12420P
Accession Date: 20181214

The invention claimed is:

1. A method of treating primary biliary cirrhosis (PBC) or primary sclerosing cholangitis (PSC), the method comprising administering a composition comprising a *Leuconostoc citreum* WiKim0104 strain having accession number KCCM12420P and having the nucleic acid sequence of SEQ ID NO: 1 as an active ingredient to a subject in need thereof.

2. The method of claim 1, wherein the composition is administered by oral administration or parenteral administration.

3. The method of claim 2, wherein the parenteral administration is intravenous injection, subcutaneous injection, intramuscular injection, intraperitoneal injection, intradermal administration, topical administration, intranasal administration, intrapulmonary administration or intrarectal administration.

* * * * *